US 9,386,360 B2

(12) United States Patent
Sagan et al.

(10) Patent No.: US 9,386,360 B2
(45) Date of Patent: Jul. 5, 2016

(54) TELEMETRY ARRANGEMENTS FOR IMPLANTABLE DEVICES

(71) Applicants: Didier Sagan, San Diego, CA (US); Steven Arroyo, Pasadena, CA (US)

(72) Inventors: Didier Sagan, San Diego, CA (US); Steven Arroyo, Pasadena, CA (US)

(73) Assignee: MiniPumps, LLC., Pasadena, CA (US)

( * ) Notice: Subject to any disclaimer, the term of this patent is extended or adjusted under 35 U.S.C. 154(b) by 0 days.

(21) Appl. No.: 14/593,607

(22) Filed: Jan. 9, 2015

(65) Prior Publication Data

US 2015/0194052 A1    Jul. 9, 2015

Related U.S. Application Data

(60) Provisional application No. 61/925,318, filed on Jan. 9, 2014.

(51) Int. Cl.
*G08C 19/16* (2006.01)
*H04Q 9/00* (2006.01)

(52) U.S. Cl.
CPC ........................................ *H04Q 9/00* (2013.01)

(58) Field of Classification Search
CPC .............................. H04B 5/0037; H04B 5/0093
USPC .......................................................... 340/12.5
See application file for complete search history.

(56) References Cited

U.S. PATENT DOCUMENTS

| 5,240,382 A * | 8/1993 | Bessho | H02K 44/06 310/11 |
| 2004/0046552 A1 | 3/2004 | Taherian et al. | |
| 2011/0115753 A1 | 5/2011 | Katsurahira | |
| 2012/0283700 A1 | 11/2012 | Pawluk | |
| 2013/0082814 A1 * | 4/2013 | Markowski | H01F 30/06 336/215 |
| 2013/0140945 A1 * | 6/2013 | Adams | F25B 21/00 310/306 |
| 2013/0158642 A1 | 6/2013 | McDonald et al. | |

FOREIGN PATENT DOCUMENTS

JP    2013-98927 A    5/2013

OTHER PUBLICATIONS

PCT International Patent Application No. PCT/US2015/010842, International Search Report and Written Opinion mailed Apr. 28, 2015, 11 pages.

* cited by examiner

*Primary Examiner* — Don N Vo
(74) *Attorney, Agent, or Firm* — Morgan, Lewis & Bockius LLP

(57) ABSTRACT

In various embodiments, a system for receiving wireless power includes a magnetic core and a plurality of layers of electrical conductors wrapped around the magnetic core. Each electrical conductor includes a first endpoint and a second endpoint; the first endpoint and the second endpoint are electrically connected to a circuit to provide power thereto, and two of the electrical conductors are electrically insulated from each other between the first endpoint and the second endpoint.

7 Claims, 9 Drawing Sheets

TELEMETRY ARRANGEMENTS FOR IMPLANTABLE DEVICES

CROSS-REFERENCE TO RELATED APPLICATION

This application claims priority to and the benefit of U.S. Provisional Application No. 61/925,318, filed on Jan. 9, 2014, the entire disclosure of which is hereby incorporated by reference.

BACKGROUND

As patients live longer and are diagnosed with chronic and often debilitating ailments, the result will be an increase in the need to place protein therapeutics, small-molecule drugs and other medications into targeted areas throughout the body that are currently inaccessible or inconvenient as sites of administration. For example, many vision-threatening diseases, including retinitis pigmentosa, age-related macular degeneration (AMD), diabetic retinopathy, and glaucoma, are incurable and yet difficult to treat with currently available therapies: oral medications have systemic side effects; topical applications may sting and engender poor compliance; injections require a medical visit, can be painful and risk infection; and sustained-release implants must typically be removed after their supply is exhausted (and offer limited ability to change the dose in response to the clinical picture). Another example is cancer, such as breast cancer or meningiomas, where large doses of highly toxic chemotherapies such as rapamycin or irinotecan (CPT-11) are administered to the patient intravenously, resulting in numerous undesired side effects outside the targeted area.

Implantable drug delivery systems, which may have a refillable drug reservoir, cannula and check valve, etc., allow for controlled delivery of pharmaceutical solutions to a specified target. This approach can minimize the surgical incision needed for implantation and avoids future or repeated invasive surgery or procedures. Refillable ocular drug pumps, for example, usually hold less than 100 µL, are much smaller and more difficult to access post-implantation than other implantable pumps, such as those used for intrathecal injections or insulin therapy.

An implantable drug-delivery pump may incorporate telemetry to facilitate communication with an external monitoring device and wireless charging of the battery powering the implanted device via inductive coupling. In particular, the operating parameters of the implantable pump may be non-invasively adjusted and diagnostic data may be read out from the implantable pump to the external monitoring device through signals transmitted by and received from the telemetry device. During a scheduled visit, a physician may place the monitoring device near the implantable pump and send signals thereto. The implant, in turn, adjusts pump parameters and transmits responses to the monitoring device. By incorporating wireless charging technology, electronic medical implants benefit from a smaller total footprint by reducing the battery size.

Typically, the telemetry circuitry comprises a coil antenna that transmits and receives signals via inductive coupling. A number of parameters characterizing the efficiency of the coil antenna, e.g., the resonant frequency, gain, quality (Q) factor, and thermal effects (i.e., the Joule effect or heat) are considered when selecting or designing the coil antenna. However, the challenges of designing an antenna small enough to fit within an implant while exhibiting adequate performance characteristics, notwithstanding tissue attenuation that weakens the inductive link, are considerable.

SUMMARY

In various embodiments, the present invention relates to telemetry coils, circuits, and related manufacturing techniques. The present invention is applicable to a wide variety of implanted devices including pacemakers, medicine-delivery pumps, stimulation devices, and artificial hearts. For illustrative purposes, the description that follows will generally focus on the use of the invention within devices having small footprints, e.g., electrolysis-actuated, implantable drug-delivery pumps as described, for example, in U.S. Ser. No. 12/463,251 (filed May 8, 2009), the entire disclosure of which is hereby incorporated by reference.

Accordingly, in a first aspect, the invention relates to a system for receiving wireless signals. In various embodiments, the system comprises a magnetic core and a plurality of layers of unbraided electrical conductors wrapped around the magnetic core, wherein each unbraided electrical conductor comprises a first endpoint and a second endpoint, the first and second endpoints being electrically connected to a circuit to provide the signal thereto, at least two of the unbraided electrical conductors being electrically insulated from each other between the first endpoint and the second endpoint and interleaved in the first layer.

In some embodiments, the first layer surrounds the magnetic core and a second layer surrounds the first layer, the second layer consisting of a single electrically connected wire. The circuit may, for example, control an implantable medical device. In various embodiments, the second endpoint comprises a tap and another unbraided electrical conductor is electrically connected between the second endpoint and a third endpoint. The unbraided electrical conductors between the first and second endpoints and between the second and third endpoints may receive energy from a primary winding and the unbraided electrical conductors between the first and second endpoints provide the signal to the circuit.

In another aspect, the invention relates to a method of operating an implantable medical device including control circuitry and, electrically connected thereto, a telemetry coil comprising a magnetic core and a plurality of layers of unbraided electrical conductors wrapped around the magnetic core, wherein each unbraided electrical conductor comprises a first endpoint and a second endpoint, the first and second endpoints being electrically connected to a the circuitry, at least two of the unbraided electrical conductors being electrically insulated from each other between the first endpoint and the second endpoint and interleaved in the first layer. In various embodiments, the method comprises the steps of wirelessly transmitting, via inductive coupling, a signal to the telemetry coil; and causing the control circuitry to operate the medical device based at least in part on the signal.

In some embodiments, the first layer surrounds the magnetic core and a second layer surrounds the first layer, the second layer consisting of a single electrically connected wire. The second endpoint may comprise a tap and another unbraided electrical conductor may be electrically connected between the second endpoint and a third endpoint. In various embodiments, unbraided electrical conductors between the first and second endpoints and between the second and third endpoints receive energy from a primary winding and the unbraided electrical conductors between the first and second endpoints provide the signal to the circuit. The signal may be a power signal delivering power to the circuit.

In another aspect, the invention pertains to a system for receiving wireless signals. In various embodiments, the system comprises a magnetic core having an axial extent and a plurality of layers of electrical conductors wrapped around the magnetic core and extending axially therealong, the electrical conductors each comprising a first endpoint and a second endpoint, the first and second endpoints being electrically connected to a circuit to provide the signal thereto. The electrical conductors are arranged in a sequence of coil elements alternating between first and second configurations along the axial extent. The first and second configurations are mirror images of each other, and each of the coil elements is electrically connected to an adjacent coil element.

In some embodiments, each of the coil configurations includes an inner open ring and an outer open ring. The inner open ring of a first coil element having the first configuration is electrically connected, across an insulator, to the outer open ring of a second coil element (having the second configuration) adjacent thereto, and the outer open ring of the first coil element is electrically connected, across the insulator, to the inner open ring of the second coil element. Adjacent coil elements may be rotated with respect to each other to accommodate electrical connections therebetween. The circuit may control an implantable medical device.

Yet another aspect of the invention relates to a method of operating an implantable medical device including control circuitry and, electrically connected thereto, a telemetry coil comprising a magnetic core having an axial extent and a plurality of layers of electrical conductors wrapped around the magnetic core and extending axially therealong, the electrical conductors each comprising a first endpoint and a second endpoint, the first and second endpoints being electrically connected to a circuit to provide the signal thereto, wherein the electrical conductors are arranged in a sequence of coil elements alternating between first and second configurations along the axial extent, the first and second configurations being mirror images of each other, each of the coil elements being electrically connected to an adjacent coil element. In various embodiments, the method comprises the steps of wirelessly transmitting, via inductive coupling, a signal to the telemetry coil and causing the control circuitry to operate the medical device based at least in part on the signal.

Each of the coil configurations may include an inner open ring and an outer open ring, wherein (i) the inner open ring of a first coil element having the first configuration is electrically connected, across an insulator, to the outer open ring of a second coil element adjacent thereto, the second coil element having the second configuration, and (ii) the outer open ring of the first coil element is electrically connected, across the insulator, to the inner open ring of the second coil element. Adjacent coil elements may be rotated with respect to each other to accommodate electrical connections therebetween.

Still another aspect of the invention relates to a method for manufacturing a coil. In various embodiments, method comprises creating a first polymer layer on a substrate; depositing a metal layer on the first polymer layer; patterning the first metal layer to form inner and outer conducting coils; depositing a second polymer layer on the patterned first metal layer; patterning the second polymer layer to open a metal-interconnection portion of the first metal layer; and depositing a second metal layer on the patterned second polymer layer, wherein the second metal layer contacts the opened metal interconnection portions of the first metal layer.

The term "substantially" or "approximately" means ±10% (e.g., by weight or by volume), and in some embodiments, ±5%. The term "consists essentially of" means excluding other materials that contribute to function, unless otherwise defined herein. Nonetheless, such other materials may be present, collectively or individually, in trace amounts. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

The foregoing will be more readily understood from the following detailed description of the invention, in particular, when taken in conjunction with the drawings, in which.

DETAILED DESCRIPTION

Figure 1:
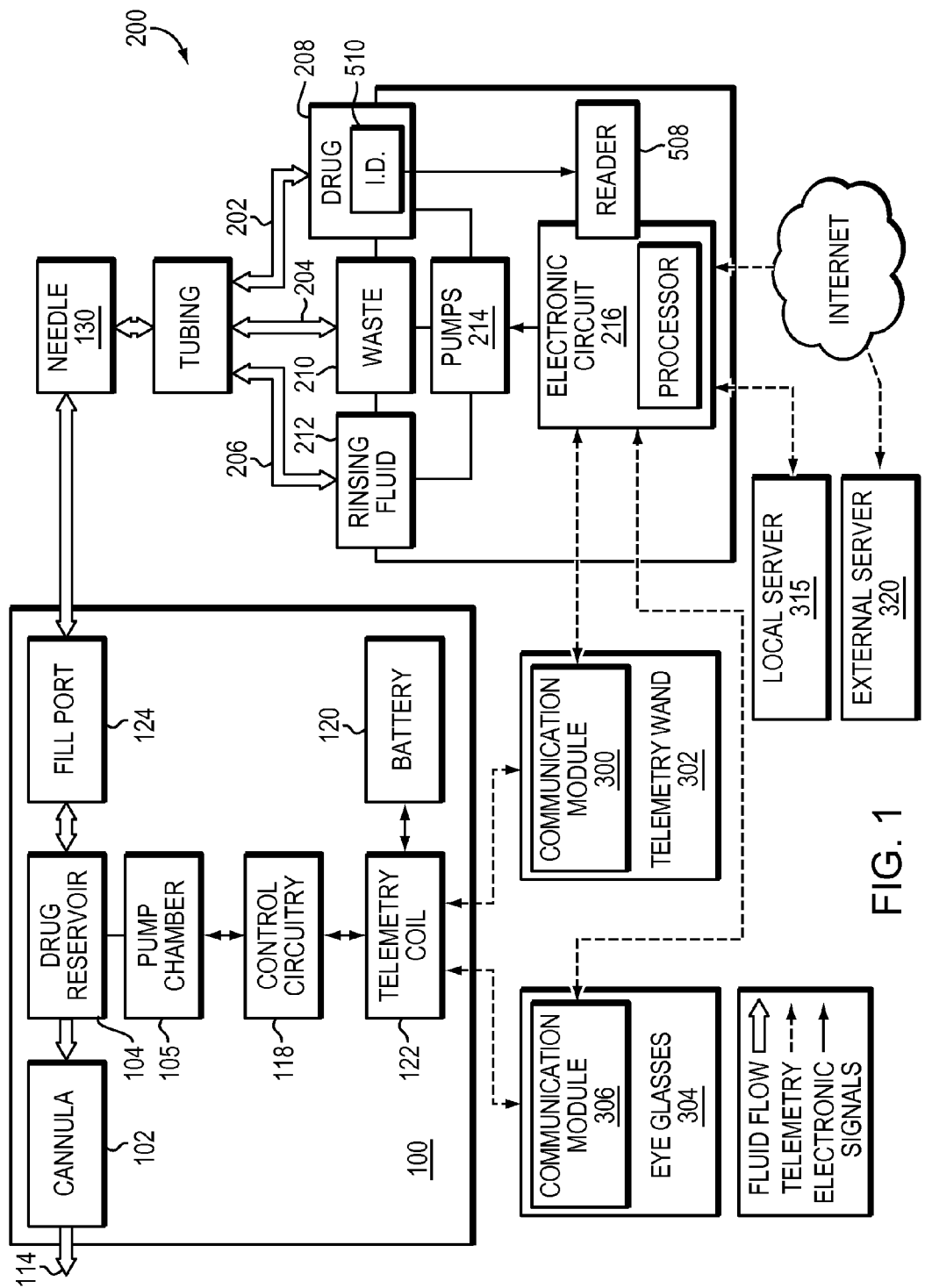
FIG. 1 illustrates a system that includes a drug-delivery pump in accordance with embodiments of the present invention.

FIG. 1 illustrates an exemplary system involving a drug-delivery pump 100. The drug pump device 100 includes a cannula 102 and a pair of chambers 104, 106. The top chamber 104 defines a drug reservoir that contains the drug to be administered in liquid form, and the bottom chamber 106 contains a liquid which, when subjected to electrolysis using electrolysis electrodes 110, evolves a gaseous product. The two chambers are separated by a corrugated diaphragm (not shown). The cannula 102 connects the top drug chamber 104 with a check valve 114 inserted at the site of administration. Control circuitry 118, a battery 120, and an induction coil 122 for power and data transmission are embedded within the device 100. Depending on the complexity of the control functionality it provides, the control circuitry 118 may be implemented, e.g., in the form of analog circuits, digital integrated circuits (such as, e.g., microcontrollers), or programmable logic devices. In some embodiments, the control circuitry 118 includes a microprocessor and associated memory for implementing complex drug-delivery protocols. The drug pump device 100 may also include various sensors (e.g., pressure and flow sensors) for monitoring the status and operation of the various device components, and such data may be logged in the memory for subsequent retrieval and review.

Importantly for the prolonged use of the drug pump device 100 following implantation, the device 100 includes one or more fill ports 124 in fluid communication with the drug reservoir 104, which permit a refill needle 130 to be inserted therethrough. The refill port 124 may define an aperture through the wall of the reservoir 104, which may be closed and sealed with a septum or plug made of a puncturable, self-sealing material, allowing a non-coring needle 130 (e.g., a needle that does not remove any of the material it punctures) to pierce through the septum while ensuring that the septum reseals itself, or "heals," upon removal of the needle. Preferably, the self-sealing material is biocompatible and able to withstand multiple punctures by the needle. The septum or plug may be made of any of a variety of elastomeric polymers (such as, e.g., silicone, polydimethylsiloxane (PDMS), polyurethane, polyethylene, parylene C, or rubber), and the specific composition of the polymer mixtures may be chosen so as to enhance the self-sealing properties. Silicone, for example, is naturally self-healing, but this property is more pronounced in particular formulations well-known to persons of skill in the art. The septum material may be injected directly into the aperture of the port and cured in place. In some embodiments, a slit is pre-formed in the septum, and the needle is inserted along this slit; the septum and surrounding port walls are sized such that radial pressure from the walls of the port compresses the septum and, with it, the slit, preventing leakage during filling and after the needle has been removed.

Through the refill port 124, the existing fluid in the reservoir (such as any residual drug) can be removed, the reservoir washed, and a filling/refilling solution injected. Certain embodiments of the invention involve an external refill system 200 that can be interfaced to the drug reservoir for the automatic filling/refilling of the reservoir 104. The refill system 200 generally includes at least two channels: one channel 204 for aspirating fluid (e.g., expired and/or remnant drug) from the reservoir of the drug pump device 100 and another channel 202 for loading new drug into the reservoir. In some embodiments, the system further includes a third channel 206 for rinsing the drug pump prior to filling it with the fresh drug. Each channel is fluidically connectable to a depot or container, e.g., one containing the drug to be dispensed (208), one receiving waste liquid from the drug pump device 100 (210), and one containing the rinsing solution (212). This rinsing solution may be the drug vehicle (e.g., a fluid missing the active ingredient, but otherwise having the same composition as the liquid drug), or any solution compatible with the drug and drug pump device 100.

The refill system 200 also includes one or more pumps 214 for generating positive or negative pressure to effect the infusion and suction of liquid into and out of the drug pump device 100. The pumps 214 may be standard mechanical pumps (e.g., gear, diaphragm, peristaltic, or syringe pumps), or pneumatic systems such as, e.g., vacuum generators, air compressors, pneumatic motors, pneumatic actuators, etc. In some embodiments, pressure sensors, flow sensors, and/or valves are integrated into the channels 202, 204, 206 and/or the pumps 214 to facilitate monitoring of the flow rate and/or pressure during the refilling process and controlling pump operation based thereon. The refill system 200 further includes electronic control circuitry 216 that directs the operation of the pump(s), and/or a user interface that allows a user (e.g., a physician or nurse) to provide input to the control circuitry 216 and/or to manually trigger certain pre-defined pump functions (e.g., via buttons, a foot pedal, and/or a conventional computer user interface including, e.g., a screen, keyboard, and mouse). The electronic control circuitry is conventional and typically comprises a processor for performing computations related to the pump operation. The processor may be a general-purpose or special-purpose processor, and may utilize any of a wide variety of data-processing and control technologies, including, e.g., a microcomputer, mini-computer, mainframe computer, programmed microprocessor, microcontroller, peripheral integrated circuit element, CSIC (customer-specific integrated circuit), ASIC (application-specific integrated circuit), logic circuit, digital signal processor, programmable logic device such as an FPGA (field-programmable gate array) or PLA (programmable logic array), RFID processor, or smart chip.

The refill system 200 may be implemented as a single unit or, alternatively, as multiple components. In certain embodiments, the pumps 214, control circuitry 216, and (optionally) valves and sensors are integrated into a reusable base unit, whereas the fluid channels 202, 204, 206 are provided in a replaceable and/or disposable tubing set connectable to the base unit and, at the other end, to the refill needle 130.

In some embodiments, one or more of the containers 208, 210, 212 holding the drug, waste liquid, and rinsing solution are provided in the form of vials or cartridges (hereinafter used synonymously). The waste-liquid cartridge 210 (or other container) may contain a dye that changes the color of the waste liquid upon contact to a noxious or at least noticeably anomalous hue such as black so as to prevent users from inadvertently re-injecting waste drug back into the patient or pump. The dye may, e.g., consist of natural or synthetic dyestuffs that are contained in the cartridge in powder form or line the surface of the cartridge. Furthermore, the cartridge 310 may contain reactive agents that disable use of the drug by destroying its activity, e.g., via an acid-base reaction, but which are non-toxic so as to avoid harm to the patient should the mixture be re-injected.

The refill system 200 may have receiving wells or other receptacles for the cartridges 208, 210, 212. In certain embodiments, the cartridges have a proprietary shape that must mate with a complementary receiving well in the refill system. This approach can also facilitate mechanical locking of the cartridge to the drug refill system, e.g., so that it snaps into place. Mechanical locking may be accomplished, e.g., using a trapezoid, triangle, or hexagonal male connector on the drug refill system and a geometrically complementary connector on the cartridge. Using cartridges of a particular shape in conjunction with matching receiving wells may serve to prevent non-proprietary cartridges or drugs from being used with the refill system 200, e.g., to ensure the integrity of the drug. A further level of security may be obtained by facilitating electronic communication between the cartridge and the refill system 200. For example, the cartridge may have a barcode encoding the identity of the drug therein, and the refill system 200 may be equipped to read the barcode once the cartridge is introduced. Alternatively, the cartridge may have an optical, RF, or similar ID tag or other electronic information storage (e.g., a ROM or an EPROM) that specifies the contents of the cartridge, and which is interrogated by the refill system 200.

In various embodiments, the refill system 200 facilitates wireless communication with the drug pump device 100. For example, the control circuitry 216 unit may include a radio-frequency (RF) transceiver or similar component that exchanges data with the induction coil 122 embedded in the pump device 100. In some embodiments, a communication or telemetry module 300 (including a transceiver and related circuitry) is provided separately from the control circuitry 216, e.g., in a handheld telemetry wand 302 that allows the operator (e.g., a nurse or physician) to conveniently bring the wand in the vicinity of the implanted pump device 100, thereby reducing power requirements on the device 100 and, consequently, its footprint. The wand may be corded to the refill system 200 or may communicate therewith via a separate wireless connection. In some embodiments, special eyeglasses 304 equipped with a telemetry module 306 are used to recharge the pump's battery 120 via the induction coil 122; such eyeglasses are described in U.S. Ser. No. 12/463,251, filed on May 8, 2009, the entire disclosure of which is hereby incorporated by reference. These eyeglasses 304 and the refill system 200 may be connected to each other or to a common console, and wireless data exchange with the drug pump device 100 may occur via the eyeglasses rather than a separate telemetry wand 302.

Via the telemetry module (of the telemetry wand 302 or the eyeglasses 304), the base unit may send refill information, including, e.g., the type of drug, the volume injected into the reservoir, a drug dosing schedule, and the date of refill, to the pump device 100. The drug pump device 100 may store this information in its on-board memory, preferably in encrypted form to ensure patient privacy, and may provide it when later interrogated by the refill system or other wireless device. The previous refill information may be used to ensure that the refill drug—as determined by the refill system's electronic label reader 508 from the barcode, RFID, optical ID, EPROM, or other electronic label 510 of the cartridge, or from the proprietary shape of the cartridge—matches the previously administered drug, thereby preventing off-label or other improper uses of the pump. Alternatively or additionally, the pump device 100 may be programmed to accept only a particular drug, and when wireless communication is established between the refill system 300 and the pump device 100, the refill system 300 and the pump exchange information to ensure that the refill drug matches the drug for which the pump was programmed. In either embodiment, refill is prevented—typically by disabling operation of the refill system—if a match is not registered. Of course, it may sometimes be necessary or desirable to change the drug administered to the patient, e.g., if a previously used drug caused complications. In this case, the operator may override the control signal that prevents the refill from commencing and/or reprogram the drug pump device 100 for the new drug.

The communication link established between the drug pump device 100 and the refill system 200 may also be used to download a stored drug dosing log or the pump operation history (including, e.g., information about any error conditions that have occurred in the pump device 100 since the previous communication) from the drug pump device 100. This information may be displayed on a screen (e.g., of a computer console that is part of the user interface) prior to commencement of the refill procedure, enabling the physician to detect any problems with the operation of the device 100 and relate the patient's condition to drug administration over extended periods of time. The physician may, for example, have the option to display twelve months of pump history or ten years of drug delivery history. Further, the physician may reprogram the drug pump device 100 at the time of refill, e.g., to adjust dosage protocols in response to changes in the patient's condition or new insights derived from medical research. In some embodiments, communication between the drug pump device 100 and the refill system 200 is sustained during the refill procedure to facilitate monitoring the process based on sensor readings acquired in the pump device 100. For example, sensors may continuously measure the pressure and fill stage of the drug reservoir 104, and send this data to the refill system 200, where it provides feedback to the processor of the control circuitry 216 and/or a physician manually controlling the refill system 200.

The data exchanged with the drug pump device 100 may be stored on a local server 315 integrated with or connected to the drug refill system 200. Alternatively, the communication module may permit the refill system 300 to communicate with an external server 320, e.g., remotely via the Internet. For example, the refill system 200 may have Wi-Fi, Zigbee, or a cellular phone chip (GSM, CDMA) that is constantly activated to cellular service or other wireless capability. This permits patient and drug data to be stored outside the refill system 300 ("in the cloud"), and may provide further levels of security and operational flexibility.

As noted earlier, the design of the telemetry coil 122 can present significant challenges, including overcoming the "skin effect" (i.e., a high current density only near the surface or "skin" of the coil conductors at high frequencies) that attenuates energy collected thereby. One approach to mitigating the skin effect is a type of cable called Litz wire, which is a braided or stranded wire that minimizes AC impedance by maximizing the conductive cross-section at a given operating frequency; as a result, Litz wire reduces skin-effect losses, and may be wrapped around a magnetic material (e.g., a ferrite core) to create an inductive coil with increased magnetic flux density. Litz wire typically consists of multiple wire strands insulated electrically from each other. Unfortunately, conventional Litz wire using a braided configuration is typically too large for use in many implant devices. For example, in a representative ocular implant, the height size restriction is less than 150 μm including wire insulation. Furthermore, some wire gauges are unsuitable as the benefit of the Litz wire in reducing the skin effect disappears once the skin depth is greater than the radius of the wire in accordance with the following equation:

$$\delta = \sqrt{\frac{2}{\omega \mu \sigma}}$$

where δ is the skin depth, ω is the angular frequency of the current, μ is the material permeability, and σ is the material conductivity.

In conventional Litz wire, the strands are insulated from each other (otherwise all the wires in the bundle would short together, behave like a single large wire, and thereby fail to mitigate the skin effect). Furthermore, the strands cannot occupy the same radial position in a bundle, since the electromagnetic effects that cause the skin effect would otherwise still disrupt conduction. The weaving or twisting pattern of the Litz wire is designed so that the individual strands are on the outside of the bundle for a distance (where the electromagnetic field changes are smaller and the strand sees low resistance), and are inside for a distance (where the field changes are the strongest and the resistance is higher). If each strand has a comparable impedance, current is distributed equally among every strand within the cable.

Figure 2A:
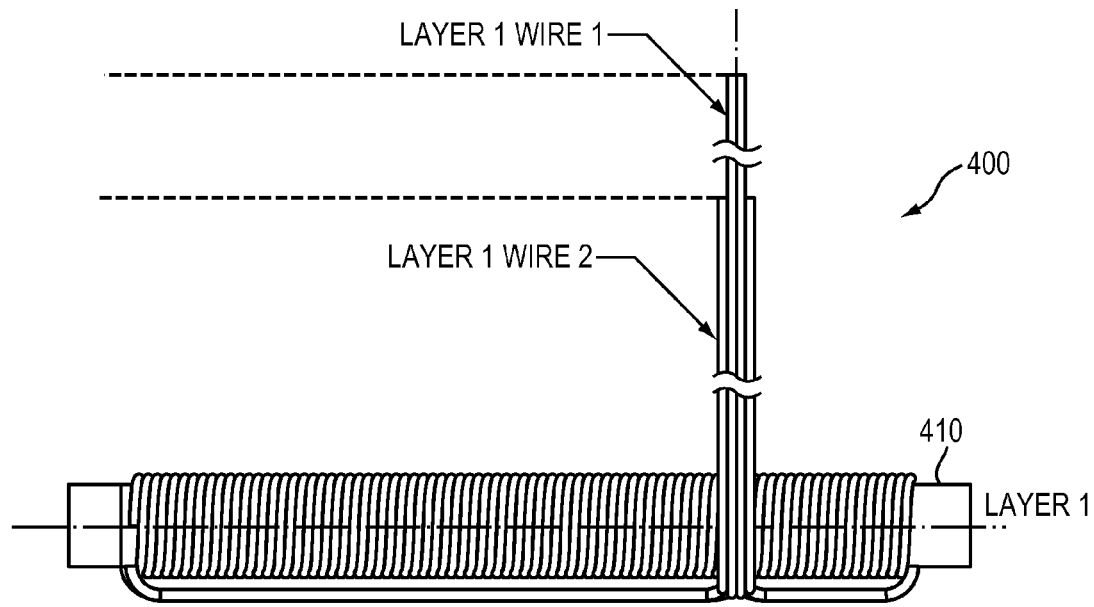
FIGS. 2A and 2B illustrate a coil having wires wrapped in a pseudo-Litz configuration in accordance with embodiments of the present invention.
Figure 2B:
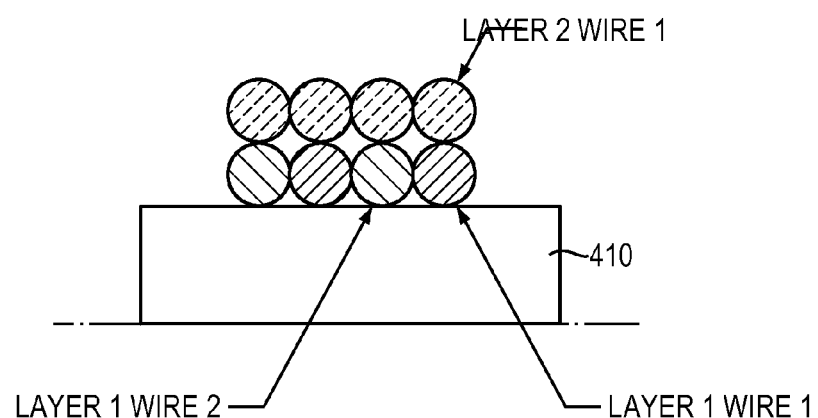

FIGS. 2A and 2B illustrate a substitute for Litz wire in accordance with an embodiment of the present invention; these are sometimes referred to herein as "pseudo-Litz" wires in that they address the skin effect without the cumbersome configuration of a traditional Litz wire. Thus, rather than a bundle, the conductor 400 utilizes two or more wire strands (wire 1 and wire 2 in the figure) in parallel that are wound side-by-side, in a single layer, around a magnetic core 410 such that the strands are of equal length; that is, as shown in FIG. 2B, wire 1 and wire 2 alternate in a single layer (layer 1). A second layer consisting of as few as a single wire (layer 2, wire 1) is wound around layer 1, wires 1 and 2. Each of the wires is insulated and has a radius greater than its skin depth at a desired operating frequency or range of frequencies. It is found that this pattern of winding mitigates or avoids skin-effect losses compared to single core winding without the need for elaborate Litz braiding that would make the wire too thick to use in an implant.

Figure 3:
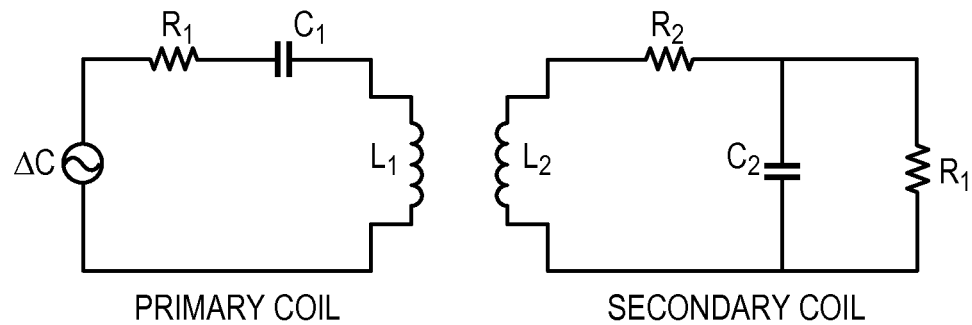
FIG. 3 illustrates a schematic diagram of an existing primary/secondary coil telemetry system.

This winding pattern affords use of an innovative voltage-divider circuit in control circuitry 118. In a conventional circuit, shown in FIG. 3, a primary coil (which would be deployed in the telemetry wand 302 and/or eyeglasses 304) includes an AC source, a capacitor $C_1$, and an inductor $L_1$. $R_1$ denotes the resistive loss in $L_1$. The secondary coil (which would be deployed in the implant 100) includes an inductor $L_2$ (which would serve as the telemetry coil 122), a capacitor $C_2$, and $R_3$ (the load of the system). $R_2$ denotes the resistive loss in $L_2$.

Figure 4:
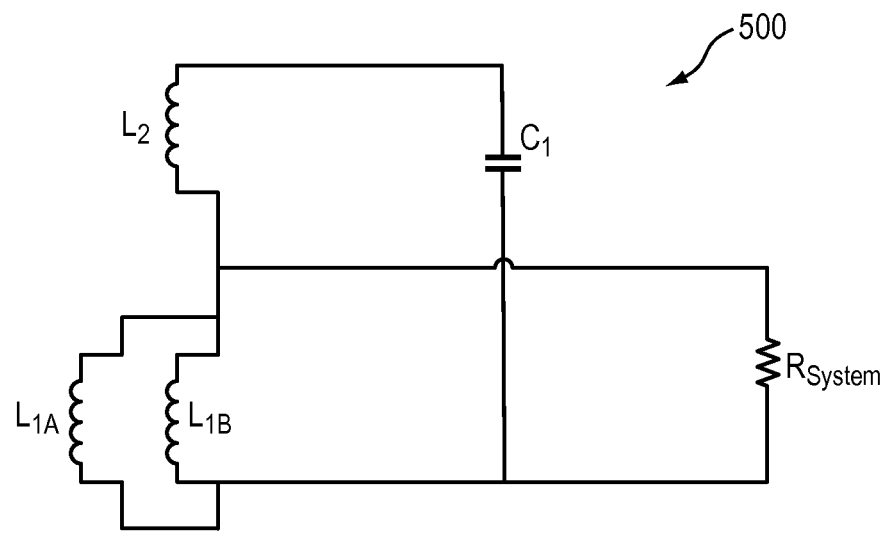
FIG. 4 illustrates a schematic diagram of a voltage divider circuit in accordance with embodiments of the present invention.

In the alternative secondary-coil circuit 500 shown in FIG. 4, the two first-layer wires of the arrangement shown in FIGS. 2A and 2B form two parallel coils $L_{1A}$, $L_{1B}$. The layer 2 winding forms a third coil $L_2$ in series with the parallel coils $L_{1A}$, $L_{1B}$. A tap is taken between the parallel coils $L_{1A}$, $L_{1B}$ and the third coil $L_2$ and run through the circuitry 118—that is, a communication module if the signal is modulated to convey information, or the battery 120 if the signal is used to recharge it—which behaves as a load $R_{system}$. The voltage across the system load is dictated by the number of turns in $L_2$ relative to $L_{1A}$, $L_{1B}$, which can of course be set for a given application. The tap point may be placed at either end of the core 410 or anywhere therealong.

In the circuit 500, the entire coil ($L_{1A}$, $L_{1B}$, and $L_2$) contributes to the resonance of the circuit, allowing for a higher loaded Q factor (maximization of self-inductance and low series resistance). However, the implant's circuitry $R_{system}$ is subjected to the lower voltage dictated by the tap, so that circuitry 118 benefits from lower impedance. Despite the voltage division which results in a voltage drop of $R_{system}$ unloaded, it is largely compensated by the resonant voltage increase. It results in a gain as the loaded Q is maintained.

In one implementation, the wire arrangement 400 and the circuit 500 were used to obtain current-voltage (IV) parameters suitable for operation of a particular implantable device. There is a minimum operating voltage as well as a maximum operating voltage as defined by the load as well as a maximum load current.

Figure 5:
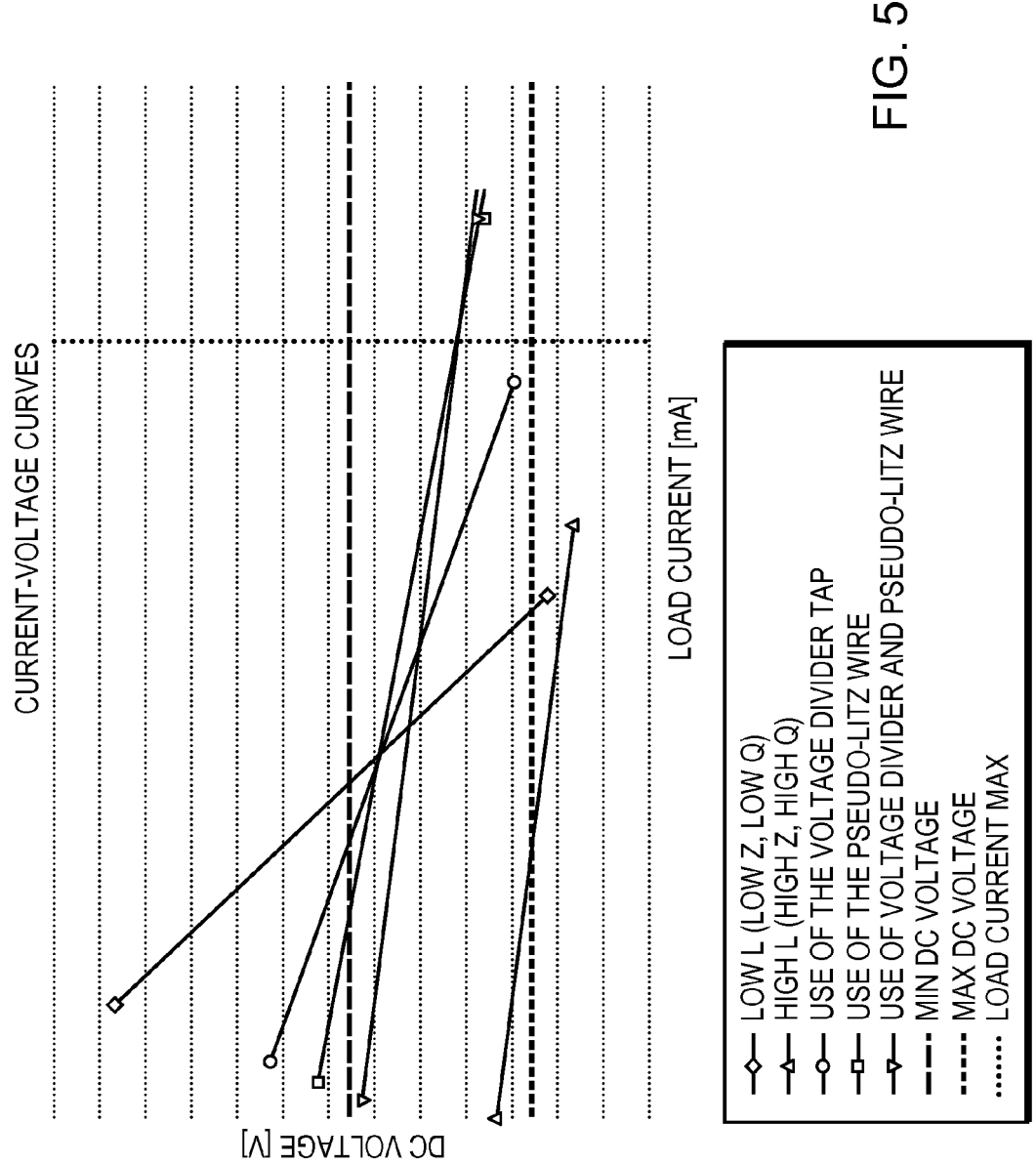
FIG. 5 illustrates current-voltage curves of the performance of embodiments of the present invention.

Conventional coils with sizes constrained by volume limitations impose a compromise between inductance, Q factor and impedance. These characteristics can be difficult to match to a particular device or application. Using the present approach, the IV curve fits within the operating parameters of the device. In FIG. 5, the IV curves produced from different combinations are compared, and demonstrate that judicious selection of the core dimensions, number and configuration of windings, winding topology, and tap position, a telemetry coil with a high Q factor and advantageous loaded IV characteristics may be created.

Figures 6A, 6B:
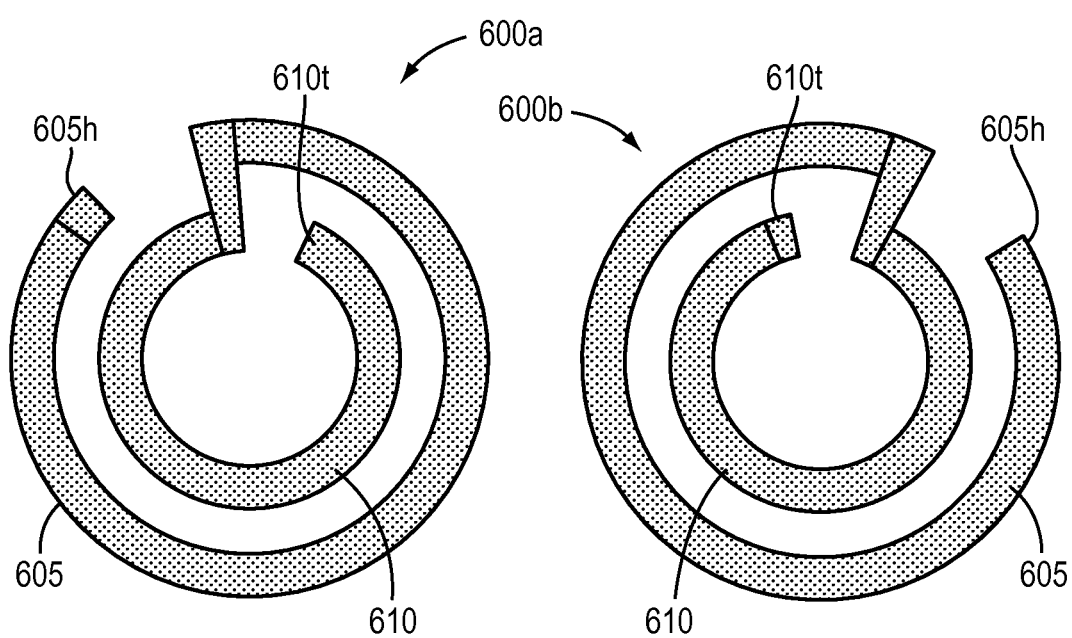
FIGS. 6A and 6B illustrate cross-sectional views of coil layers in accordance with embodiments of the present invention.
Figure 7:
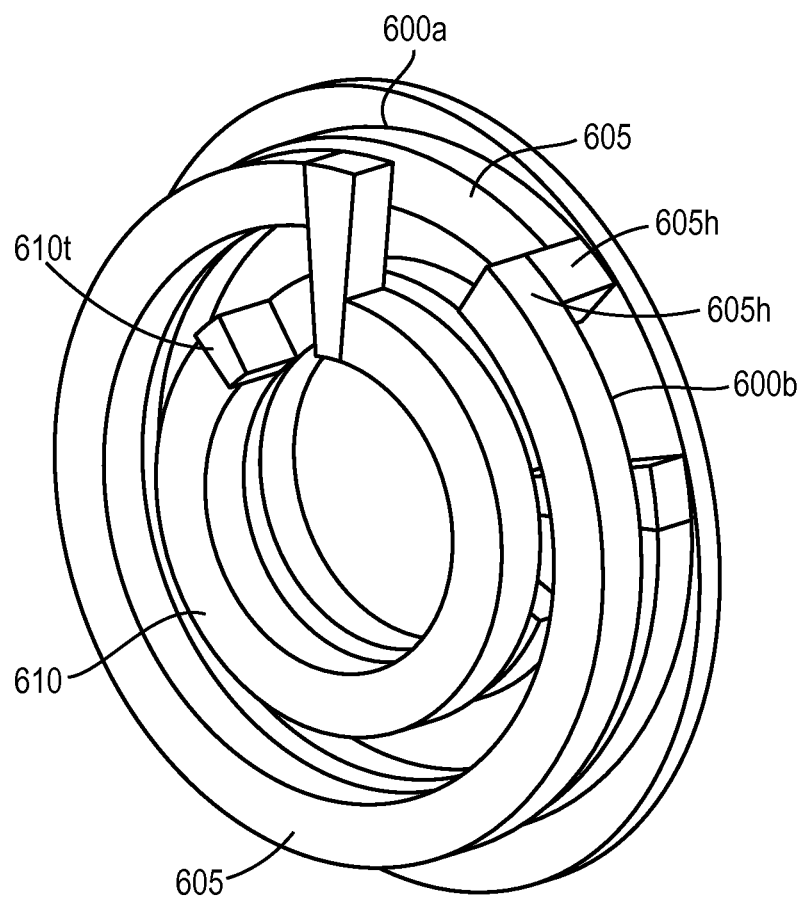
FIG. 7 illustrates a three-dimensional view of coil layers in accordance with embodiments of the present invention.
Figure 8:
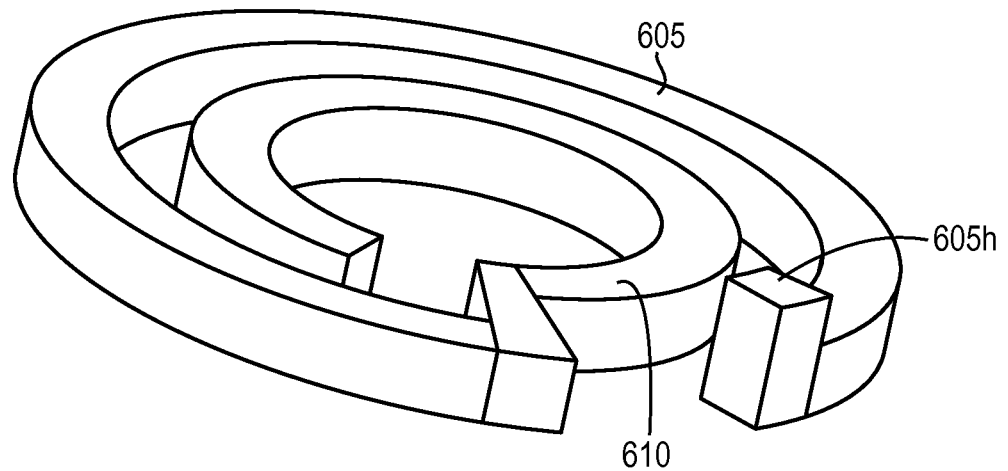
FIG. 8 illustrates a perspective view of a coil layer in accordance with embodiments of the present invention.

Another approach to skin-effect mitigation uses, instead of wires, conductive traces that may be printed or otherwise deposited onto a substrate. The basic pattern 600 is illustrated in FIGS. 6A, 6B, and 7, and consists of a series of interconnected outer ring elements 605 and inner ring elements 610. FIGS. 6A and 6B illustrate coil elements 600a, 600b that are mirror images of each other and serve as adjacent coil layers in a sequence of such layers; the coil layers alternate between the two mirror-opposite configurations 600a, 600b along an axis (e.g., surrounding an axial magnetic core). Each layer 600 comprises or consists of an outer ring element, which has a head end 605h in the form of a tab, and an inner ring having a tail end 610t. With reference to FIGS. 7 and 8, an insulating disk 615 intervenes between adjacent coil layers, and the coil elements 600a, 600b are connected across (i.e., traverse) the disk 615 so that the proximal coil element 600b on a first side of the insulating disk 615 electrically connects thereacross to the distal coil element 600a on the opposite side of the disk 615. Similarly, for the next connection, the distal coil element 600a electrically connects, across another insulating disk, to a coil element 600b. FIGS. 7 and 8 illustrate the three-dimensional configuration of the coil elements 600 and how the head and/or tail ends terminate in transversely extending tabs that may be connected to an adjacent coil element through the insulating disk. A tab may be connected to the tab of an adjacent coil element or to a flat head or tail portion thereof.

Figure 9A:
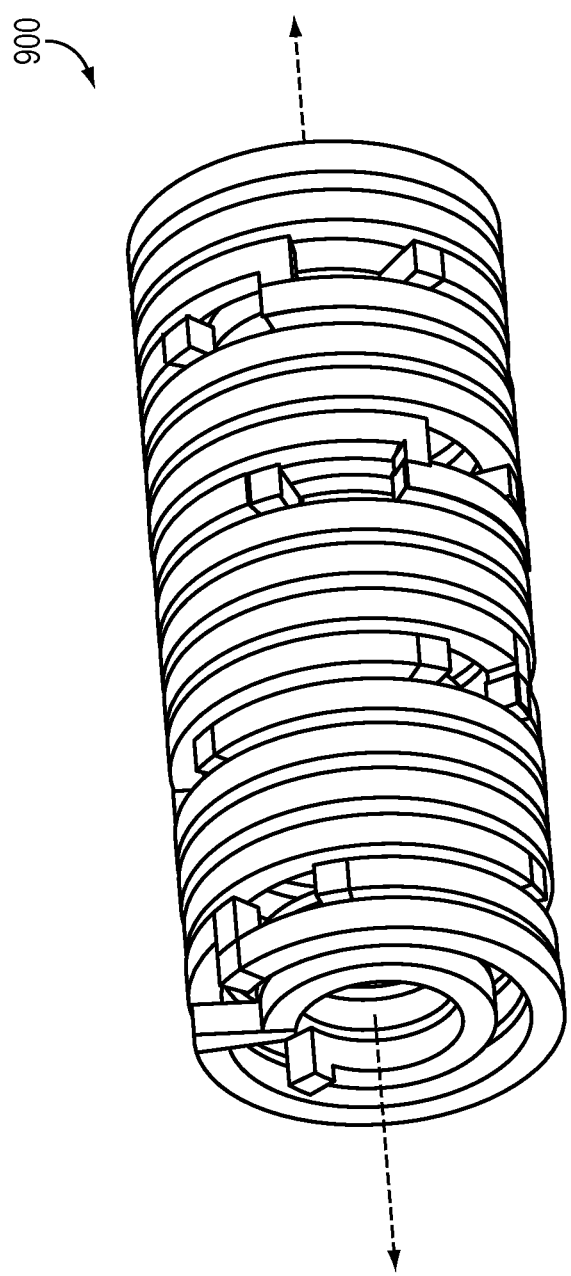
FIGS. 9A and 9B illustrate three-dimensional views of coil layers in accordance with embodiments of the present invention.
Figure 9B:
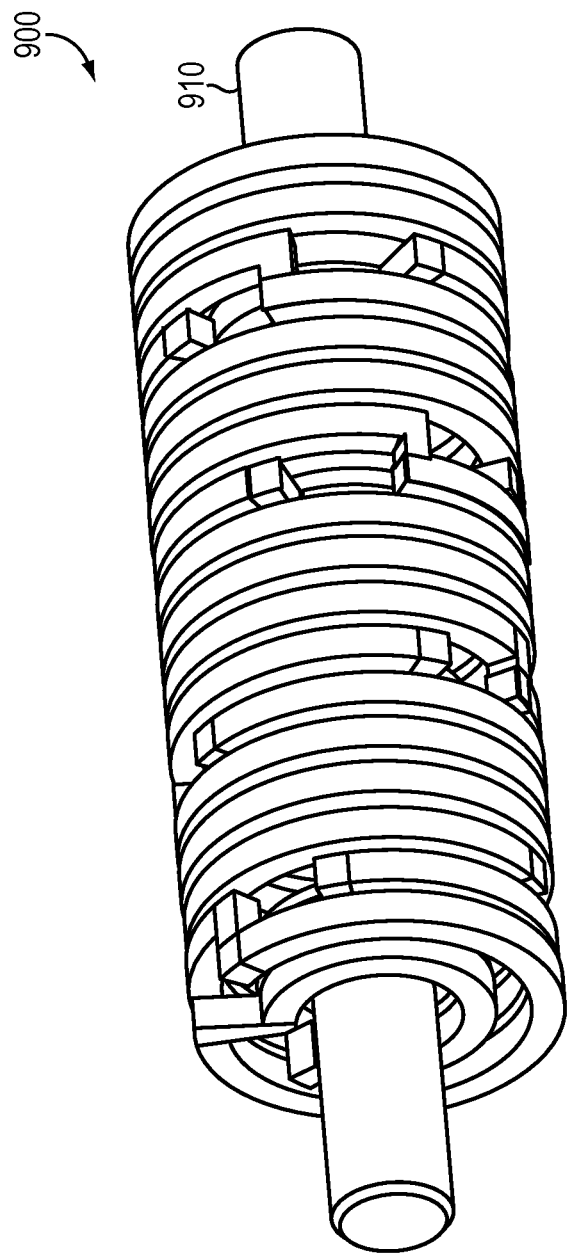

Alternatively, if creation of internal vias to facilitate the interconnection is difficult, interconnects may extend radially over the edge of the disk 615. In that case (as shown in FIG. 9A), when this pattern is extended axially to create a coil 900 consisting of a linear series of coil elements, the head and tail ends shift circumferential positions the by a preset angle along the axial extent of the resulting coil structure 900. This preset angle is ideally minimized to increase the representative equivalent of "coil winding length" without compromising the insulative properties between coil elements. FIG. 9B illustrates that the coil structure 900 can surround a magnetic (e.g., ferrite) core 910, which serves to increase the magnetic field and thus the inductance. The resulting coil structure 900 may be further encapsulated in an epoxy, resin, and/or glass tubing to completely insulate it for use in an implantable medical device.

The arrangement 700 has various advantages compared with conventional Litz wire. First, it may contain more wire turns or coils in a compact form, as insulation coatings surrounding wires are unnecessary. A second advantage is that the minimal interconnect thickness may allow for more coils over a given axial length. A third advantage is the convenience, reproducibility and accuracy achievable with deposition techniques.

Pseudo-Litz wires in accordance herewith may be created in layers using microelectromechanical (MEMS) fabrication technology. A representative sequence of fabrication steps includes or consists of creating a first polymer layer on a substrate; depositing a metal layer on the first (polymer) layer; patterning the first metal layer to form the inner and outer helices; depositing a second polymer layer on the patterned first metal layer; patterning the second polymer layer to open the metal interconnection portion of the first metal layer; and depositing a second metal layer on the patterned second polymer layer, so that the second metal layer contacts the opened metal interconnection portions of the first metal layer. These steps are repeated until the desired configuration is reached. The telemetry coil may be completed in sections, with multiple sections combined to create the desired coil size. The metal may comprise, consist, or consist essentially of gold, copper, or any conductive metal. The polymer layer may be polyimide, parylene, polyesters, polydimethylsiloxane (PDMS) or other non-conductive materials.

Alternatively, pseudo-Litz wires may be created in layers using PCB or Flex technology. For example, traces may be deposited or printed (e.g., by screen printing) onto a flexible substrate such as polyimide, or may be applied using photolithography, or coil layers may be laminted between substrate sheets.

Having described certain embodiments of the invention, it will be apparent to those of ordinary skill in the art that other embodiments incorporating the concepts disclosed herein may be used without departing from the spirit and scope of the invention. For example, various features described with respect to one particular device type and configuration may be implemented in other types of devices and alternative device configurations as well. Accordingly, the described embodiments are to be considered in all respects as only illustrative and not restrictive.

What is claimed is:

1. A system for receiving wireless signals, the system comprising:
    a magnetic core having an axial extent; and
    a plurality of layers of electrical conductors wrapped around the magnetic core and extending axially therealong, the electrical conductors each comprising a first endpoint and a second endpoint, the first and second endpoints being electrically connected to a circuit to provide the signal thereto, wherein the electrical conductors are arranged in a sequence of coil elements alternating between first and second configurations along the axial extent, the first and second configurations being mirror images of each other, each of the coil elements being electrically connected to an adjacent coil element.

2. The system of claim 1 wherein each of the coil configurations includes an inner open ring and an outer open ring, wherein (i) the inner open ring of a first coil element having the first configuration is electrically connected, across an insulator, to the outer open ring of a second coil element adjacent thereto, the second coil element having the second configuration, and (ii) the outer open ring of the first coil element is electrically connected, across the insulator, to the inner open ring of the second coil element.

3. The system of claim 2, wherein adjacent coil elements are rotated with respect to each other to accommodate electrical connections therebetween.

4. The system of claim 1, wherein the circuit controls an implantable medical device.

5. A method of operating an implantable medical device including control circuitry and, electrically connected thereto, a telemetry coil comprising a magnetic core having an axial extent and a plurality of layers of electrical conductors wrapped around the magnetic core and extending axially therealong, the electrical conductors each comprising a first endpoint and a second endpoint, the first and second endpoints being electrically connected to a circuit to provide the signal thereto, wherein the electrical conductors are arranged in a sequence of coil elements alternating between first and second configurations along the axial extent, the first and second configurations being mirror images of each other, each of the coil elements being electrically connected to an adjacent coil element, the method comprising the steps of:
    wirelessly transmitting, via inductive coupling, a signal to the telemetry coil; and
    causing the control circuitry to operate the medical device based at least in part on the signal.

6. The method of claim 5 wherein each of the coil configurations includes an inner open ring and an outer open ring, wherein (i) the inner open ring of a first coil element having the first configuration is electrically connected, across an insulator, to the outer open ring of a second coil element adjacent thereto, the second coil element having the second configuration, and (ii) the outer open ring of the first coil element is electrically connected, across the insulator, to the inner open ring of the second coil element.

7. The method of claim 6, wherein adjacent coil elements are rotated with respect to each other to accommodate electrical connections therebetween.

* * * * *